United States Patent [19]

Purifoy et al.

[11] Patent Number: 5,079,235
[45] Date of Patent: Jan. 7, 1992

[54] ANTIVIRAL COMPOUNDS

[75] Inventors: Dorothy J. M. Purifoy; Saad G. Rahim, both of Beckenham, England

[73] Assignee: Burroughs Wellcome Co., Research Triangle Park, N.C.

[21] Appl. No.: 465,552

[22] Filed: Jan. 16, 1990

Related U.S. Application Data

[63] Continuation of Ser. No. 132,478, Dec. 14, 1987, abandoned.

[30] Foreign Application Priority Data

Dec. 15, 1986 [GB] United Kingdom ............... 8629892

[51] Int. Cl.$^5$ .................. A61K 31/70; C07H 17/00
[52] U.S. Cl. ............................ 514/49; 514/50; 536/24
[58] Field of Search ................. 514/23, 49, 50

[56] References Cited

U.S. PATENT DOCUMENTS

| | | | |
|---|---|---|---|
| 4,267,171 | 5/1981 | Bergstrom et al. | 536/23 |
| 4,274,544 | 1/1981 | Bergstrom et al. | 536/23 |
| 4,863,906 | 9/1989 | Rahim et al. | 514/50 |

FOREIGN PATENT DOCUMENTS

| | | | |
|---|---|---|---|
| 0082667 | 6/1983 | European Pat. Off. | |
| 0082668 | 6/1983 | European Pat. Off. | 530/23 |
| 0095294 | 11/1983 | European Pat. Off. | |
| 0097039 | 12/1983 | European Pat. Off. | 536/23 |

OTHER PUBLICATIONS

Goodchild et al., J. Med. Chem., 26, 1252–1257 (1983).
DeClercq, "Approaches to Antiviral Agents", Editor, Harnden, 1985.
DeClercq et al., J. Med. Chem., 26(5), pp. 661–666 (1983), Nucleic Acid Related Compounds, 40, Synthesis and Biological Activities of C-Alkynyluracil Nucleosides.
Giziewicz et al., Canadian J. Chem., pp. 147–151, vol. 62 (1984), The Crystal and Molecular Structure of 5-(-propyn-1-yl)-1-($\beta$-D-arabinofuranosyl)uracil.
Balzarini et al., Methods and Find Exptl. Clin. Pharmacol, 7(1), 1985, pp. 19–28, Incorporation of 5-Substituted Pyrimidine Nucleoside Analogues into DNA of a Thymidylate Synthetase-Deficient Murine FM3A Carcinoma Cell Line.
Chem. Abs., vol. 91, 1979, pp. 26–27.
J. Med. Chem., 1984, 27(3), pp. 410–412.
Febs. Symp., 1979, 57, pp. 275–285.
Biochem. Pharmacol., 1983, 32(4), pp. 726–729.
Nucleic Acids Symp. Ser., 1981, 9, pp. 103–106.
Antimicrobial Agents Chemother., 1980, 17(6), pp. 1030–1031.
Antiviral Research, 1981, 1(4), pp. 213–223.
Nucleosides and Nucleotides, 1986, 5(5), pp. 571–578.
Antiviral Research, 4(3), pp. 159–168, 1984.
Int. Congr. Ser. Excerpta. Med. Herpes Virus Clin. Pharmacol. Basic Aspects, pp. 211–214, 1982.
Acta. Microbiol. Acad. Sci. Hung., 1981, 28(3), pp. 307–312.
Antiviral Chemother. Des. Inhib. Viral Function, 1981, Proc. Symp. Antiviral Chemotherap., pp. 207–217.
Antimicrob. Agents, 23(3), pp. 416–421, 1983.
Mol. Pharmacol. (1982), 21, pp. 217–223.
Nucleic. Acids Res. Spec. Pub. (1978), 4, pp. 103–106.

*Primary Examiner*—John W. Rollins
*Attorney, Agent, or Firm*—Donald Brown

[57] ABSTRACT

The present invention relates to certain novel 5-substituted pyrimidine nucleosides and pharmaceutically acceptable derivatives thereof and their use in the treatment of varicella zoster virus, cytomegalovirus and Epstein Barr virus infections. Also provided are pharmaceutical formulations and processes for the preparation of the compounds according to the invention.

24 Claims, No Drawings

ANTIVIRAL COMPOUNDS

This is a continuation of copending application Ser. No. 07/132,478, filed on Dec. 14, 1987, now abandoned.

The present invention relates to novel pyrimidine nucleosides and their use in medical therapy particularly for the treatment of herpes virus infections.

Of the DNA viruses, the herpes group is the source of the most common viral illnesses in man. The group consists of herpes simplex virus (HSV), varicella zoster (VZV), cytomegalovirus (GMV) and Epstein-Barr virus (EBV).

Varicella zoster virus (VZV) is a herpesvirus which causes chicken-pox and shingles. Chicken-pox is the primary disease produced in a host without immunity and in young children is usually a mild illness characterised by a vesicular rash and fever. Shingles or zoster is the recurrent form of the disease which occurs in adults who were previously infected with varicella-zoster virus. The clinical manifestions of shingles are characterised by neuralgia and a vesicular skin rash that is unilateral and dermatomal in distribution. Spread of inflammation may lead to paralysis or convulsions. Coma can occur if the meninges become affected. In immunodeficient patients VZV may disseminate causing serious or even fatal illness. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host and, following a primary infection, virus may be shed for a number of years. Clinical effects range from death and gross disease (microcephaly, hepatosplenomegaly, jaundice, mental retardation) through failure to thrive, susceptibility to chest and ear infections to a lack of any obvious ill effect. CMV infection in AIDS patients is a predominant cause of morbidity as; in 80% of the adult population, it is present in a latent form and can be re-activated in immuno-compromised patients. Epstein-Barr virus (EBV) causes infectious mononucleosis, and is also suggested as the causative agent of nasopharyngeal cancer, immunoblastic lymphoma, Burkitt's lymphoma and hairy leukoplakia.

Attention has focussed on nucleoside analogues for the treatment of herpes viral infections. One compound, originally of interest as a useful intermediate, is 2'-deoxy-5-ethynyluridine, the synthesis of which is disclosed by Barr et al. (J. Chem. Soc. Perkin Trans. I (1978), 1263). This compound was tested for antiviral activity in vitro against vaccinia and herpes simplex for example as described by Walker et al (Nucleic Acid Res., Special Pub. No. 4, 1978) and in U.S. Pat. Specification No. 4424211 but did not demonstrate any effect of use in human medicinal chemotherapy U.S. Pat. No. 4,863,906 describes and claims the use of 2'-deoxy-5-ethynyluridine and its pharmaceutically acceptable derivatives in the treatment of human virus infections caused by cytomegalovirus (CMV) or varicella zoster virus (VZV).

We have now surprisingly discovered that certain other novel pyrimidine nucleosides characterised by the presence of an unsaturated grouping in the 5-position are of particular value in medical therapy particularly for the treatment of certain viral infections as described below. These compounds also have the advantage that they have been found to possess a relatively low level of toxicity as determined by cell culture toxicity experiments in vitro.

The novel pyrimidine nucleosides referred to above may be represented by the following general formula (I):

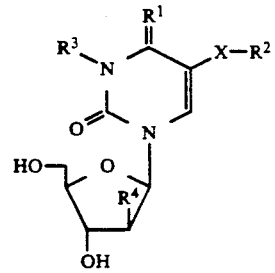

wherein X represents a vinylene or ethynylene group, $R^1$ represents an oxo or imino group; $R^2$ represents hydrogen or a $C_{1-2}$ alkyl or a C3-4 branched or cycloalkyl group e.g. isopropyl or cyclopropyl; $R^3$ represents a hydrogen atom or an acyl e.g. $C_{1-4}$ alkanoyl or benzoyl group optionally substituted for example by one or more halogen, alkyl, hydroxy or alkoxy substituents; and $R^4$ represents a hydrogen atom or a hydroxy group provided that (a) when $R^1$ is imino, $R^3$ is hydrogen and $R^4$ is hydrogen or hydroxy, —X—$R^2$ does not represent a vinyl, ethynyl or propenyl group; (b) when $R^1$ is oxo; $R^3$ is hydrogen and $R^4$ is hydrogen or hydroxy, —X—$R^2$ does not represent a vinyl, ethynyl, 1-propenyl, 1-propynyl, 1-butenyl, 1-butynyl or 3,3,3-trimethyl-1-propynyl group; or a pharmaceutically acceptable derivative thereof.

It will be appreciated that when $R^3$ is not an acyl group, the compound of formula (I) may exist in its tautomeric form.

The above-mentioned pyrimidine nucleosides also include the pharmaceutically acceptable derivatives of such compounds, ie. any pharmaceutically acceptable salt, ester, or salt of such ester, or any other compound which, upon administration to a human subject, is capable of providing (directly or indirectly) the antivirally active metabolite or residue thereof.

Such pyrimidine nucleosides and their derivatives will be hereinafter referred to as the compounds according to the invention. Preferred compounds of formula (I) include those wherein (a) X represents an ethynylene group especially when $R^2$ represents a hydrogen atom or a methyl group.

(b) $R^3$ represents a hydrogen atom or a benzoyl group; and/or (c) $R^4$ represents a hydrogen atom especially when X represents an ethynyl group and $R^2$ represents a methyl group.

The following novel compounds are preferred compounds according to the invention particularly by virtue of their especially potent antiviral activity, particularly against VZV and in some cases CMV.

(a) 3-N-benzoyl-2'-deoxy-5-ethynyluridine
(b) 3-N-benzoyl-2'-deoxy-5-propynyluridine
(c) 2'-deoxy-5-(1-propynyl)cytidine
(d) 1-(β-D-arabinofuranozyl)-5-propynylcytosine Particularly preferred compound are b) and c) which have shown potent anti-VZV activity.

Further novel compounds of the invention include:

(j) 1-(β-D-arabinofuranozyl)-3-N-benzoyl-5-propynyluracil
(k) 1-(β-D-arabinofuranozyl)-3-N-benzoyl-5-ethynyluracil
(l) 3-N-benzoyl-2'-deoxy-5-vinyluridine
(m) 1-(β-D-arabinofuranozyl)-3-N-benzoyl-5-vinyluracil Also pharmaceutically acceptable salts and esters of such compounds The above compounds all have particularly high activity against VZV, while compound a) also has high activity against CMV.

The present invention further includes a method for the treatment of a viral infection selected from VZV, CMV and EBV infections which comprises treating a subject with an effective amount of a compound according to the invention.

Examples of the clinical conditions caused by such herpes viruses as CMV, VZV and EBV infections which may be treated in accordance with the invention include those referred to above.

Preferred mono- and di-esters according to the invention include carboxylic acid esters in which the non-carbonyl moiety of the ester grouping is selected from straight or branched chain alkyl, alkoxyalkyl (e.g. methoxymethyl), carboxyalkyl (e.g. carboxyethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl, or aralkylsulphonyl (e.g. methanesulphonyl); and mono-, di- or tri-phosphate esters which may or may not be blocked, amino acids esters and nitrate esters. With regard to the above-described esters, unless otherwise specified, any alkyl moieties present in such esters advantageously contain 1 to 18 carbon atoms, particularly 1 to 4 carbon atoms. Any aryl moiety present in such esters advantageously comprises a phenyl group. Any reference to any of the above compounds also includes a reference to a pharmaceutically acceptable salt thereof.

Salts according to the invention which may be conveniently used in therapy include physiologically acceptable base salts, eg derived from an appropriate base, such as alkali (e.g. sodium), alkaline earth metal (e.g. magnesium) salts, ammonium and $NX^{+}_{4}$ (wherein X is $C_{1-4}$ alkyl) salts.

The compounds according to the invention may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-indicated utilities and indications the amount required of the individual active ingredients will depend upon a number of factors including the severity of the condition to be treated and the identity of the recipient and will ultimately be at the discretion of the attendant physician. In general, however, for each of these utilities and indications, a suitable, effective dose will be in the range 0.1 to 250 mg per kilogram body weight of recipient per day, preferably in the range 1 to 100 mg per kilogram body weight per day and most preferably in the range 5 to 30 mg per kilogram body weight per day; an optimum dose is about 15 mg per kilogram body weight per day (unless otherwise indicated all weights of active ingredient are calculated as the parent compound; for salts and esters thereof the figures would be increased proportionately.) The desired dose may if desired be presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the compounds to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

For infections of the eye or other external tissues, e.g., mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w"w of a polyhydric alcohol, i.e. an alcohol having two or more hydroxyl groups such as propylene glycol, butane-1,3-diol, mannitol sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifer(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non- aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The compounds according to the invention may be prepared by any of the methods known in the art for the preparation of the same or similar compounds e.g. see U.S. Pat. Specification No. 4424211, or Robins M. J., and Barr, P. J., J. Org. Chem. (1983) 1854–1862, and in particular the processes described in the Examples given hereinafter.

The present invention also provides a process for the preparation of a compound according to the invention which comprises:

A. condensing a compound of formula

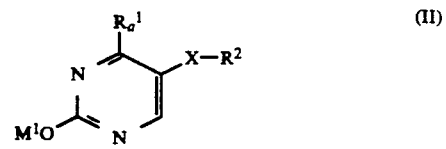

(II)

(wherein $R^2$ is as hereinbefore defined, X represents an ethynylene group, $R^1_a$ represents a protected hydroxy or amino group and $M^1$ represents a hydroxy protecting group) with a compound of formula

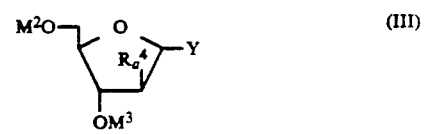

(III)

(wherein Y represents a halogen atom, $M^2$ and $M^3$ each represents a hydroxy-protecting group and $R^4_a$ represents hydrogen or a protected hydroxy group);

B. reacting a compound of formula

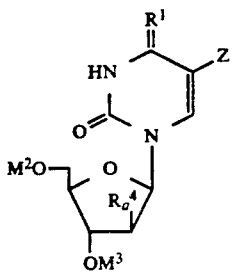

wherein $R^1$, $M^2$, $M^3$ and $R^4_a$ are as defined above and Z is a leaving group, with a compound capable of providing the necessary grouping of formula —X—$R^2$ (in which X is ethynylene and $R^2$ is as defined above) to form a compound of formula (I) in which X is ethynylene and $R^3$ is hydrogen; and, C. reacting a compound of formula

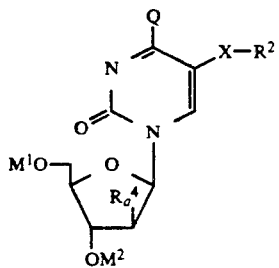

(wherein Q is an appropriate leaving group and X, $R^2$, $M^1$, $M^2$ and $R^4_a$ are as defined above) with an agent serving to replace the group Q with an amino group; to form a compound in which X is ethynylene and $R^3$ is hydrogen; and optionally thereafter or simultaneously therewith, performing either or both of the following, in any desired order:

i) removing any remaining protecting groups;

ii) where the resulting compound is a compound of formula (I), converting it into a pharmaceutically acceptable derivative thereof or, where the resulting compound is pharmaceutically acceptable derivative, converting it into a different pharmaceutically acceptable derivative or a compound of formula (I).

With regard to process A), the starting materials may be protected with conventional protecting groups such as acyl groups, e.g. alkanoyl or aroyl groups such as p-toluoyl, or triakylsilyl groups such as the trimethylsilyl group, the $M^1$ and $R^1_a$ protecting groups being generally silyl protecting groups. The halogen group Y of the sugar residue (formula (III)) is conveniently chlorine and the reaction carried out in the presence of a Lewis acid catalyst, for example stannic chloride, in a appropriate solvent, such as 1,2-dichloroethane. The parent compound can then be obtained, following anomeric separation, by treatment with alcoholic base, such as sodium methoxide in methanol. This process is also described by Barr, et al., in J. Chem. Soc., Perkin Trans 1 (1978), 1263 et seq.

The protecting groups can subsequently be removed by acid or base hydrolysis, acyl groups being advantageously removed by base hydrolysis and silyl groups by acid hydrolysis.

Regarding process B), this is exemplified by Robins, M. J., and Barr, P. J., in J. Org. Chem. (1983), 48, 1854 et seq. A 5-halogenated nucleoside such as 2'-deoxy-5-iodouridine in a suitably protected form, for example with the protecting groups referred to above, can be subjected to a catalysed coupling reaction, for example with a palladium catalyst, with an appropriate protected acetylene, such as trimethylsilylacetylene, in the presence of an organic base, such as triethylamine, and another metal catalyst, for example a copper (I) salt, at an elevated temperature such as 50° C. to give the protected acetylenic nucleoside. A preferred palladium catalyst is bis(triphenylphosphine)palladium dichloride and a preferred copper catalyst is cuprous iodide. The parent compound can readily be obtained by removal of any protecting groups for example by treatment with alcoholic base, such as sodium methoxide in methanol.

In process C), the leaving group Q is advantageously a suitable heterocyclyl group advantageously a 1,2,4-triazol-1-yl group or a halo e.g. chloro group, the removal of the group Q being suitably effected by treatment of the compound of formula (V) with ammonia.

The compound of formula (V) may be prepared for example by treating the corresponding 4-oxo compound with an appropriate functionalising agent serving to introduce the leaving group Q for example by treatment with 1,2,4-triazole, conveniently in the presence of a condensing agent such as 4-chlorophenylphosphodichloridate, e.g. in a base solvent advantageously pyridine or by treatment of the 4-oxo compound with thionyl chloride in dimethylformamide.

The above-mentioned starting materials may be prepared in conventional manner from known compounds using techniques that are known in the art for example as described in Nucleic Acid Chemistry: Improved New Synthetic Procedures, Methods and Techniques. Ed. L. B. Townsend and R. S. Tipson, Wiley Interscience (1978) and Nucleoside Analogues: Chemistry, Biology and Medical Applications Ed. R. T. Walker, E de Clercq and F. Eckstein, NATO Advanced Study Institute, Plenum Press (1979). Examples of methods for the preparation of the starting materials are described below.

In process A), the compound of formula (II) in which $R^2$ is hydrogen and X is ethynylene may be prepared, for example, by halogenating 5-acetyluracil with a suitable halogenating agent, such as phosphoryl chloride, in the presence of base to yield a compound of formula (VI)

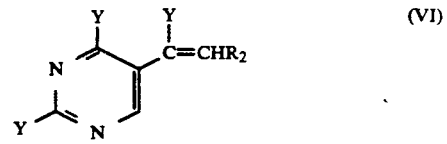

wherein Y is halogen. The compound of formula (VI) may then be further treated with an inorganic base, such as aqueous potassium hydroxide, and then protected, to yield the compound of formula (II).

In process B), the compound of formula (IV) particularly wherein Z represents a halogen atom such as iodine and $R^4_a$ represents a protected hydroxy group can be prepared for example by methods analogous to those described by Schinazi et al, J. Med. Chem, 1979, 22 (20) 1273.

The compounds of formula (I) in which X represents a vinylene group may be prepared from corresponding compounds in which X represents an ethynylene group for example by catalytic hydrogenation using an appropriate catalyst for example a Lindlar catalyst poisoned with quinoline, eg in an alcoholic solvent such as methanol or ethanol. Other methods for preparing these vinylene compounds are described for example by S. G. Rahim et al, Nucleic Acids Research 1982 10(17), 5285.

The compounds of formula (I) in which $R^3$ represents an acyl group may be prepared from corresponding compounds in which $R^3$ represents a hydrogen atom for example by selective protection of the hydroxy groups in the sugar residue, eg using trialkylsilyl groups, and subsequently acylating the protected compounds using for example the appropriate acid chloride or anhydride, advantageously in the presence of a base such as pyridine or triethylamine which may also serve as a solvent medium for the reaction. The resulting acyl compound of formula (I) may then be obtained by deprotection, eg by removal of the trialkylsilyl groups by for example treatment with an acid such as acetic acid.

Esters according to the invention may be prepared in conventional manner e.g. by treatment of the parent compound of formula (I) or an ester thereof (optionally protected) with an appropriate esterifying or transesterifying agent respectively, for example, by treatment of 2'-deoxy-5-ethynyluridine with an appropriate acid halide (e.g. chloride) or anhydride in the presence of base, conveniently pyridine, which may also be used as the solvent, any remaining protecting groups being thereafter removed.

Salts according to the invention may also be prepared in conventional manner for example by reaction of the parent compound with an appropriate base to form the corresponding base salt. Other derivatives according to the invention can also be prepared in conventional manner.

The following examples illustrate the present invention.

Example 1
3-N-Benzoyl-2'-deoxy-5-ethynyluridine

To a stirred suspension of 2'deoxy-5-ethynyluridine (J. Med. Chem., 26(5), 661-6, (1983)) (0.3 g, 1.19 mmoles) in dry acetonitrile (8 ml) and chlorotrimethylsilane (0.5 ml) was added, with ice cooling, triethylamine (0.85 ml, 6.1 mmoles) and the whole was stirred at room temperature for 2 hrs. Benzoylchloride (0.18 ml, 1.54 mmoles) was then added and the mixture stirred for a further 1.5 hrs and filtered. The filtrate was concentrated, the residue dissolved in ethanol (10 ml) and glacial acetic acid (0.4 g) was added. After stirring for 0.5 hr, the solvents were evaporated and the residue purified by column chromatography on silica gel eluting with methylene chloride/methanol (19:1) to give the title compound 0.2 g (47% yield) melting at 156°-7° C.
CHN Cal. C, 60.70,H, 4.49; N, 7.86%
Found C, 60.44; H, 4.336; N, 7.69%

Example 2 2'-Deoxy-5-propynylcytidine a) 2'-deoxy-3',5'-di-O-acetyl-5-propynyluridine 0.8 ml of acetic anhydride was added to a solution of 2'-deoxy-5-propynyluridine (J. Med. Chem., 26(5), 661-6, (1983)) (1 g, 3.76 mmol) in 10 ml of dry pyridine. The mixture was stirred at room temperature 16 hrs., then evaporated to dryness to give a foamy solid. Recrystallisation from ethanol gave 0.98 g (75%) of the title compound melting at 148°-9° C.
CHN calculated C, 54.86; H, 5.143; N, 8.00%
Found C, 54.82; H, 5.114; N, 7.805% b) 1-(2-Deoxy-3,5-di-O-acetyl-$\beta$-D-ribofuranosyl)-5-propynyl-4-(1,2,4-triazol-1-yl)pyrimidine-2(1H)-one p-Chlorophenylphosphodichloridate (0.76 g, 3.10 mmol) was added to a solution of product of stage a) (0.7 g, 2 mmol) and 0.45 g of 1,2,4-triazole (6.5 mmol) in 20 ml of dry pyridine. The solution was stirred under dry $N_2$ at room temperature for 2 days then evaporated to dryness. The resulting oil was eluted on a silica gel column with ethyl acetate to give 0.33 g of starting material and 0.2 g (44% based on 0.4 g of starting material) of the title compound, which decomposes further on standing at room temperature. This was not purified further but carried onto the next step.

c) 2'-deoxy-5-propynylcytidine

Crude product of stage b) (0.2 g, 0.5 mmol) was dissolved in 5 ml of Dioxan/880NH$_3$/H$_2$O (3:2:1) and the mixture was left standing at room temperature for 16 hrs. It was then evaporated to dryness and the residue co-evaporated with ethanol. The resulting white solid was recrystallised from ethanol to give 0.04 g (30%) of pure product decomposing at 195°-200° C.
CHN calc. C, 54.34; H, 5.60; N, 15.85%
Found C, 54.19; H, 5.550; N, 15.33%

Example 3
1-($\beta$-D-Arabinofuranozyl)-5-propynylcytosine a) $O^2$, 2'-Anhydrouridine Uridine (10 g, 0.04 mole) was dissolved in 20 ml of warm, dry dimethylformamide, and 11.4 g of diphenylcarbonate (0.06 m) and 0.2 g of sodium bicarbonate were added. The solution was stirred and heated at 150° C. until evolution of carbon dioxide ceased (30 min approx). After cooling the solution was poured into 200 ml of ether with rapid stirring. The resulting solid was filtered off, washed with ether, and recrystallised from methanol to give 7.2 g (80%) of the title compound, as white crystals, melting at 235°-40° C.

b) 1 ($\beta$-D-Arabinofuranosyl)uracil

The product of Stage a) (7.0 g, 0.03 mole) was dissolved in 585 ml of ethanol/water (1:1) and 41 ml of 1M sodium hydroxide was added. After stirring at room temperature for 2.0 hr the solution was acidified to pH 4-5 by portionwise addition of Dowex 50(H) ion exchange resin. The resin was filtered off and washed with 100 ml of ethanol/water (1:1). The filtrate was evaporated to dryness, and the residue recrystallised from ethanol, to give 5.51 g (75%) of the title compound, as white crystals, melting at 220°-3° C.

c) 1 (B-D-Arabinofuranosyl)-5-iodouracil

The product of Stage b) (3.0 g, 12.3 mmole), 3.0 g of iodine (11.8 mmole), 15 ml of chloroform, and 30 ml of 1M nitric acid were vigorously stirred and refluxed together for 2.0 hr. After cooling, a crystalline solid separated, which was filtered off, and washed thoroughly with ether to remove excess iodine. The solid was recrystallised from water to give 2.55 g (56%) of the title compound as white crystals melting at 191°-3° C. (decomp).

d) 5-Iodo-1-(2,3,5-tri-O-acetyl-β-D-arabinofuranosyl)uracil

Acetic anhydride (1.04 ml, 11 mmol) was added to a solution of 1 g of product of stage (c) (2.7 mmol) in 10 ml of dry pyridine. After stirring for 3 hours at room temperature, the solvent was evaporated and the residue was co-evaporated with $CH_2Cl_2$ several times. The CHN calc. C, 54.34; H, 5.60; N, 15.85% residue was triturated with ethanol, the solid filtered and dried to give 1.25 g (93%) of the title compound, melting at 175°-9° C.

e) 5-Propynyl-1 (2,3,5-tri-O-acetyl-β-D-arabinofuranosyl)uracil

A suspension of product of stage a) (1.16 g, 2.3 mmol), 35 mg of cuprous iodide and 35 mg of bis(triphenylphosphine)palladium (II) chloride in 95 ml of dry triethylamine was stirred under dry $N_2$ for 15 mins. Propyne gas was then bubbled through the mixture for 15 mins and the mixture was stirred under an atmosphere of $N_2$ at 50° C. for 1 hr. The solution was filtered and the filtrate evaporated to dryness. The residue was taken up in $CH_2Cl_2$ (30 ml) washed with 2×25 ml portions of 2% aqueous disodium ethylenediamine tetracetic acid solution and 50 ml of water. The organic solution was dried ($Na_2SO_4$) and evaporated and recrystallisation of the residue from ethanol gave 0.38 g (40%) of the title compound melting at 150°-157° C.

CHN calc. C, 52.94; H, 4.902; N, 6.863%
Found C, 52.86; H, 4.827; N, 6.784% f) 5-Propynyl-1-(2,3,5-tri-O-acetyl-β-D-arabinofuranosyl)-4-(1,2,4-triazol-1-yl)pyrimidin-2(1H)-one p-Chlorophenylphosphodichloridate (10.5 ml) was added to a solution of product of stage b) (0.5 g, 1.2 mmol) and 0.4 g of 1,2,4-triazole in 10 ml of dry pyridine. The solution was stirred at room temperature under an atmosphere of dry nitrogen for 6 days then evaporated to dryness. The residue was partitioned between dichloromethene (30 ml) and water (30 ml). The organic layer was washed with 25 ml of water, dried ($Na_2SO_4$) and evaporated, to give 0.65 g of crude product which was used in the next stage of the synthesis.

g) 1-(β-D-arabinofuranosyl)-5-propynylcytosine

Crude product of stage c) (0.65 g, 1.39 mmol) was dissolved in 30 ml of Dioxan/88ONH$_3$/H$_2$O (3:2:1) and the solution was left standing at room temperature overnight. The solution was evaporated to dryness to give a yellow oil which was triturated with ethanol to give the pure product (0.22 g) melting at 241°-243° C. (deomposed).

CNH Calculated for $C_{12}H_{15}N_3O_5.0.7 H_2O$ C, 49.05; H, 5.586; N, 14.30%
Found C, 49.28; H, 5.32; N, 13.95%

Example 4

3-N-Benzoyl-2'-deoxy-5-propynyluridine

Dry triethylamine (1.1 ml) was added at 0° C. to a stirred suspension of 2'-deoxy-5-propynyluridine (J. Med. Chem., 26(5), 661-6 (1983)) (0.4 g, 1.5 mmol) and 0.54 g of trimethylsilylchloride (4.97 mmol) in 10 ml of dry acetonitrile. The mixture was stirred at room temperature for 2.5 hours then 0.3 ml of benzoylchloride was added and stirring continued for a further 5 hours. A solid was filtered off, the filtrate was evaporated to dryness, the residue was taken up in ethanol and 0.4 g of acetic acid were added and the mixture was stirred at room temperature for 0.5 hours. The mixture was evaporated to dryness and the residue was eluted on a silica gel column with $CH_2Cl_2$/MeOH (9:1). Several recrystallisations from aqueous ethanol gave 0.14 g (25%) of the product, melting at 137°-140° C.

CHN calculated for $C_{19}H_{18}N_2O_6.0.2 H_2O$ C, 60.96; H, 4.920; N, 7.489%
Found C, 60.69; H, 4.681; N, 7.478%

Example 5

2'-Deoxy-5-ethynyl-3-N-(p-toluoyl)uridine

To a stirred suspension of 2'-deoxy-5-ethynyluridine (J. Med. Chem., 26(5), 661-6, (1983)) (0.4 g, 1.6 mmol) in dry acetonitrile (15 ml) and chlorotrimethyl silane (0.7 ml, 5.6 mmol) was added, with ice cooling, triethylamine (1.13 ml, 8.1 mmol) and stirring was maintained at room temperature for 2.5 hr. Toluoylchloride (0.3 ml, 2.1 mmol) was then added and after stirring for a further 7 hr the mixture was filtered, the filtrate evaporated to dryness and the residue dissolved in ethanol (20 ml). Glacial acetic acid was then added and after stirring for 0.5 hr at room temperature the solvent was evaporated and residual acetic acid coevaporated with ethanol. Purification of the product by thick layer silica chromatography eluting with methanol/methylenechloride (1:24) followed by recrystallisation from methanol afforded title compound (0.03 g) melting at 176-9° C.

CHN calculated for $C_{19}H_{18}N_2O_6.0.2$ EtOH C, 61.37; H, 5.08; N, 7.36%
Found C, 60.92; H, 4.87; N, 7.40%

The following examples illustrate pharmaceutical formulations according to the invention in which the active ingredient is a compound of formula (I).

| Example A Tablet | |
|---|---|
| Active ingredient | 100 mg |
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

| Ophthalmic Solution Example B | |
|---|---|
| Active ingredient | 0.5 |
| Sodium chloride, analytical grade | 0.9 g |
| Thiomersal | 0.001 g |
| Purified water to | 100 ml |
| pH adjusted to | 7.5 |

Example C: Tablet Formulation

The following formulations A and B are prepared by wet granulation of the ingredients with a solution of povidone, followed by addition of magnesium stearate and compression.

| | mg/tablet | mg/tablet |
|---|---|---|
| Formulation A | | |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |
| Formulation B | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Formulation C | | |
| Active ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients. The lactose used in formulation E is of the direct compression type.

| | mg/capsule |
|---|---|
| Formulation D | |
| Active Ingredient | 250 |
| Pregelatinised Starch NF15 | 150 |
| | 400 |
| Formulation E | |
| Active Ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

Drug release takes place over a period of about 6-8 hours and was complete after 12 hours.

Example D: Capsule Formulation

Formulation A

A capsule formulation is prepared by admixing the ingredients of Formulation D in Example C above and filling into a two-part hard gelatin capsule. Formulation B (infra) is prepared in a similar manner.

| | mg/capsule |
|---|---|
| Formulation B | |
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogol 4000 BP | 350 |
| | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules are prepared by dispersing the active ingredient int he lecithin and arachis oil and filling the dispersion into soft, elastic gelatin capsules.

Formulation E (controlled Release Capsule)

The following controlled release capsule formulation is prepared by extruding ingredients a, b, and c using an extruder, followed by spheronisation of the extrudate and drying. The dried pellets are then coated with release controlling membrane (d) and filled into a two-piece hard gelatin capsule.

| Example E: Injectable Formulation | |
|---|---|
| | mg/capsule |
| (a) Active Ingredient | 250 |
| (b) Microcrystalline Cellulose | 125 |
| (c) Lactose BP | 125 |
| (d) Ethyl Cellulose | 13 |
| | 513 |
| Active ingredient | .0200 g |
| Sterile, pyrogen free phosphate buffer (pH 7.0) to | 10 ml |

The active ingredient is dissolved in most of the phosphate buffer (35°-40° C.), then made up the volume and filtered through a sterile micropore filter into a sterile 10 ml amber glass vial (type 1) and sealed with sterile closures and overseals.

| Example F: Intramuscular injection | |
|---|---|
| Active Ingredient | 0.20 g |
| Benzyl Alcohol | 0.10 g |
| Glucofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

| Example G: Syrup Suspension | |
|---|---|
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

| Example H: Suppository | |
|---|---|
| | mg/suppository |
| Active Ingredient (63 μm)* | 250 |
| Hard Fat, BP (Witepsol H15 - Dynamit NoBel) | 1770 |
| | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

| Example I: Pessaries | |
|---|---|
| | mg/pessary |
| Active ingredient 63 μm | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

Antiviral and Toxicity Testing

Human cytomegalovirus (HCMV) is assayed in monolayers of either MRC5 cells (human embryonic lung) or Detroit 532 cells (human foreskin fibroblasts) in multiwell trays. Activity of compounds is determined in the plaque reduction assay, in which a cell monolayer is infected with a suspension of HCMV, and then overlaid with nutrient agarose in the form of a gel to ensure that there is no spread of virus throughout the culture. A range of concentrations of compound of known molarity was incorporated in the nutrient agarose overlay. Plaque numbers of each concentration are expressed as percentage of the control and a dose-response curve is drawn. From this curve the 50% inhibitory concentration ($IC_{50}$) is estimated.

Varicella zoster virus (VZV) is assayed in MRC5 cells by a similar method of that for HCMV with the omission of the agarose overlay.

An assay is performed in which virus-producing cells (P3HR-1) are exposed to drug for 14 days after which the EBV genome copies per cell are determined by EBV specific c-RNA-DNA hybridization. Epstein Barr virus is assayed by the methods of Nonoyama & Pagano disclosed in Nature: New Biology Vol. 233, pg. 103-4 1971. The $IC_{50}$ value given in the results is the concentration required to inhibit the EBV genome No/cell by 50%

Cell toxicity is assessed in a cell growth inhibition assay. Subconfluent cultures of Vero cells grown on 96-well microtiter dishes are exposed to different dilutions of drug, and cell viability determined daily on replicate cultures using uptake of a tetrazolium dye (MTT). The concentration required for a 50% inhibition of cell viability at 96 hours is termed $CCID_{50}$.

The results are shown in the following Table.

TABLE

| Example | $IC_{50}$ (μM) VZV | $IC_{50}$ (μM) HCMV | $CCID_{50}$ (μM) at 96 hr |
|---|---|---|---|
| 2 | 3.3 | >20 | >300 |
| 4 | 2.2 | 28.5 | >500 |

We claim:
1. A compound of formula (I)B

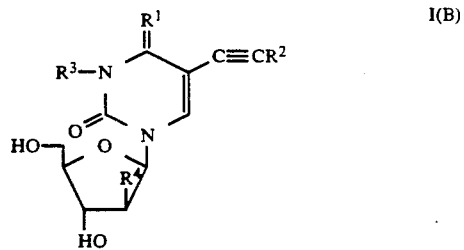

wherein $R^1$ represents an oxo or imino group; $R^2$ represents hydrogen, a $C_{1-2}$ alkyl or a $C_{3-4}$ branched or cycloalkyl group; $R^3$ represents a hydrogen atom, or $C_{1-4}$ alkanoyl or a benzoyl group optionally substituted by one or more halogen, alkyl, hydroxy or alkoxysubstitutents; and $R^4$ represents a hydrogen atom or a hydroxy group provided that (a) when $R^1$ is imino; $R^3$ is hydrogen and $R^4$ is hydrogen or hydroxy; $R^2$ does not represent a hydrogen atom or methyl group; (b) when $R^1$ is oxo; $R^3$ is hydrogen and $R^4$ is hydrogen or hydroxyl; $R^2$ does not represent a hydrogen atom, methyl, ethyl or tertbutyl group; or a pharmaceutically acceptable salt, ester or salt of such ester.

2. A compound according to claim 1 wherein $R^1$ is oxo.

3. A compound according to claim 1 or 2 wherein $R^4$ is hydrogen.

4. A compound according to claim 1 wherein $R^3$ is benzoyl.

5. The compound 3-N-Benzoyl-2'-deoxy-5-ethynyluridine.

6. The compound 2'-deoxy-5-(1-propynyl)cytidine.

7. The compound 1-(β-D-Arabinofuranozyl)-5-propynylcytosine.

8. The compound 3-N-Benzoyl-2'-deoxy-5-propynyluridine.

9. A compound according to claim 1 wherein the compound is 1-(β-D-Arabinofuranozyl)-3-N-benzoyl-5-ethynyluracil.

10. A compound according to claim 1, wherein the compound is 1-(β-D-arabinofuranozyl)-3N-5-propynyl uracil.

11. A pharmaceutical formulation suitable for use in combatting human VZV, CMV or EBV infections comprising as active ingredient, an effective VZV, CMV or EBV treatment amount of a compound according to claim 1 and a pharmaceutically acceptable carrier therefor.

12. A formulation according to claim 11 in a form for administration by injection.

13. A formulation according to claim 11 in a form of a sterile solution.

14. A formulation according to claim 11 in a form for topical administration.

15. A formulation according to claim 14 in the form of a topical ointment or cream.

16. A formulation according to claim 11 in a form for oral administration.

17. A formulation according to claim 16 in the form of a tablet or capsule.

18. A pharmaceutically acceptable salt, ester or salt of such ester of the compound 3-N-Benzoyl-2'-deoxy-5-propynyluridine.

19. A pharmaceutically acceptable salt, ester or salt of such ester of the compound 2'-deoxy-5-(1-propynyl)-cytidine.

20. A pharmaceutically acceptable salt, ester or salt of such ester of the compound 3-N-Benzoyl-2'-deoxy-5-ethynyluridine.

21. A method of treating VZM, CMV or EBV infection in a human comprising the administration to said human of an effective VZV, CMV or EBV infection treatment amount of a compound of formula I(B):

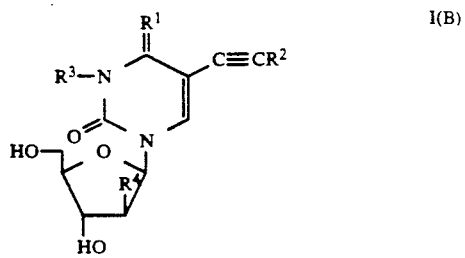

wherein $R^1$ represents an oxo or imino group; $R^2$ represents hydrogen, a $C_{1-2}$ alkyl or a $C_{3-4}$ branched or cycloalkyl group; $R^3$ represents a hydrogen atom, or $C_{1-4}$ alkanoyl or a benzoyl group optionally substituted by one or more halogen, alkyl, hydroxy or alkoxy substituents; and $R^4$ represents a hydrogen atom or a hydroxy group provided that (a) when $R^1$ is imino; $R^3$ is hydrogen and $R^4$ is hydrogen or hydroxy, $R^2$ does not represent a hydrogen atom or methyl group; (b) when $R^1$ is oxo; $R^3$ is hydrogen and $R^4$ is hydrogen or hydroxy; $R^2$ does not represent a hydrogen atom, methyl, ethyl or tertbutyl group; or a pharmaceutically acceptable salt, ester or salt of such ester.

22. A method according to claim 21 wherein said infection is a CMV infection.

23. A method according to claim 21 wherein said infection is a VZV infection.

24. A method according to claim 21 wherein said infection is a EBV infection.

* * * * *